United States Patent [19]

Pham

[11] Patent Number: 5,030,232

[45] Date of Patent: Jul. 9, 1991

[54] NASAL IMPLANT DEVICE WITH IMPROVED CONTOUR

[76] Inventor: Van H. Pham, 19 Bayborte, Irvine, Calif. 92714

[21] Appl. No.: 600,265

[22] Filed: Oct. 22, 1990

Related U.S. Application Data

[63] Continuation of Ser. No. 334,296, Apr. 6, 1989, abandoned.

[51] Int. Cl.$^5$ ............................................. A61F 2/18
[52] U.S. Cl. ..................................... 623/10; D24/155
[58] Field of Search ................. 623/10; D24/33, 99; 606/196

[56] References Cited

U.S. PATENT DOCUMENTS

| D. 263,747 | 4/1982 | Jaramillo et al. | 128/342 |
| D. 270,759 | 9/1983 | Straith | 623/10 |
| 3,935,859 | 2/1976 | Doyle | 128/342 |
| 4,201,201 | 5/1980 | Vergara | 128/342 |

FOREIGN PATENT DOCUMENTS 0748326 4/1956 United Kingdom ................ 128/342

OTHER PUBLICATIONS

"Porex Medical Profile: Silicon Facial Implants", Porex Medical a division of Porex Technologies Corp. of Georgia, p. 2.

Primary Examiner—Randall L. Green
Assistant Examiner—Stephanie L. Iantorno

[57] ABSTRACT

The nasal implant of this invention is characterized by a composition of hard-grade silicone fashioned into a special shape. One variation in the composition material is to use soft silicone only for the tip in order to overcome the fear of some surgeons to use hard silicone in this particular area.

A special and improved shape of the implant, in the form of a modified hourglass, provides a well rounded and larger tip portion thanb that of the prior art. The supra-tip of this improved implant shows a depression dorsally, is less wide than the rest of the implant and has a pronounced slope laterally. These features, particularly at the supra-tip region avoid the unnatural effects of the prior art devices. Moreover this implant has a variable thickness form upper end to tip -that is it starts thin, increases in thickness and then goes thinner again- whereas the prior art starts thin and continually increases throughout.

7 Claims, 2 Drawing Sheets

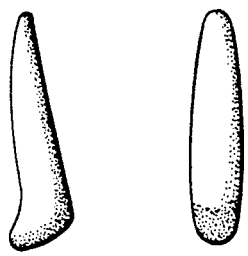
FIG. 1A  FIG. 1B
PRIOR ART  PRIOR ART
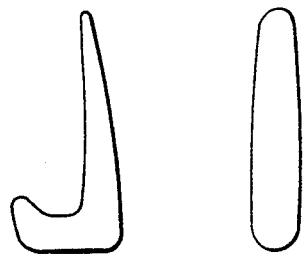
FIG. 2A  FIG. 2B
PRIOR ART  PRIOR ART
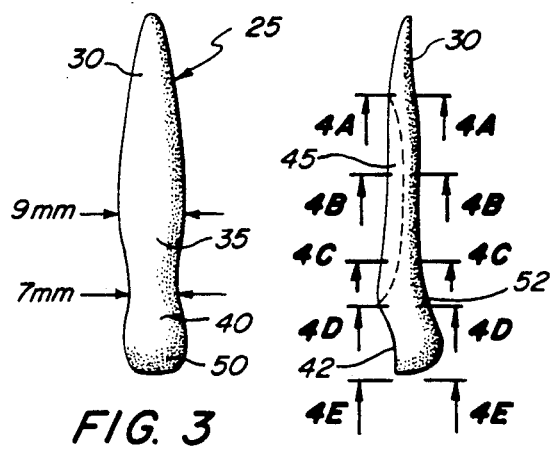
FIG. 3  FIG. 4
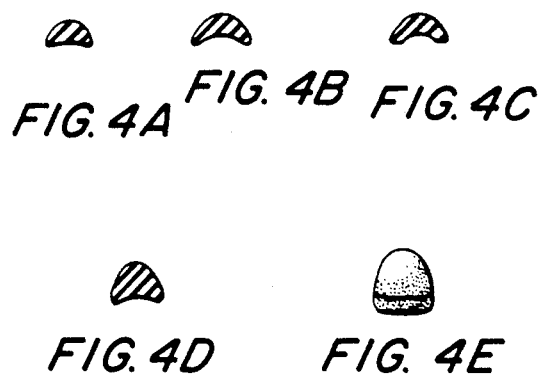
FIG. 4A  FIG. 4B  FIG. 4C
FIG. 4D  FIG. 4E
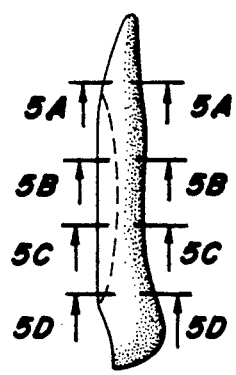
FIG. 5
FIG. 5A  FIG. 5B  FIG. 5C  FIG. 5D

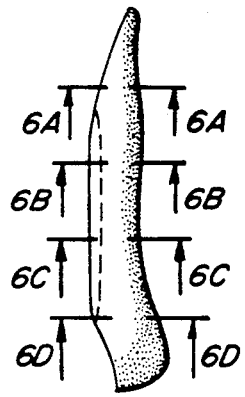
FIG. 6 FIG. 6A FIG.6B FIG.6C FIG.6D
FIG. 7   FIG. 8

NASAL IMPLANT DEVICE WITH IMPROVED CONTOUR

This is a continuation application of my pending U.S. application entitled NASAL IMPLANT DEVICE WITH IMPROVED CONTOUR, having Ser. No. 07/334,296 filed on Apr. 6, 1989, and abandoned subsequent to this application.

BACKGROUND OF THE INVENTION

People often require aesthetic surgery to the nose in order to obtain a more pleasing appearance. This invention relates to a nasal implant as part of such aesthetic surgery. Successful alteration of the shape of the nose requires a nasal implant that is natural looking and which is not noticeable under the skin when the implant is in place and the healing is completed.

1. Field of the Invention

The field of this invention relates to nasal implant devices and more particularly relates to natural looking implant devices.

2. Description of the Prior Art

There have been prior art implants in the market for some time now. One particular company that has supplied nasal implants is Porex Medical a division of Porex Technologies Corp. of America. Suppliers, such as Porex, offer a wide variety of implant shapes to accommodate the many different shapes and sizes of human noses. All of the prior art implants known to the inventor are made from a soft silicone material. This soft material is natural feeling but suffers from a lack of support near the tip of the implant; and in most instances their shape, particularly at the tip area, contributes to an unnatural look.

All of the prior art devices known to the inventor are defined by, or at least include, essentially straight line portions. For example, when such devices are looked at in a plan view the implant device has straight line sides. At the tip of the nose location for some prior art implants a slightly raised portion to help define the forward bulbous portion of the patient'nose. Other prior art implant do not have the raised portion and instead have a tip to lip return portion at the forward end of the implant. The implant in this latter instance resembles an L in side view with the shorter part of the L being inserted into the columella, that is the area between the tip and the lip.

These and other prior art implants all suffer from the same shortcomings. In general the implants give to the corrected nose an unnatural look. Primarily the unnatural look can be attributed to what is termed a parrot's beak (supra-tip higher than the tip) and secondarily the width of the implant at the upper end is too wide and too straight. Also, in most prior art devices the supra-tip is the same width as the rest of the implant's body so that the implant does not blend well with the patient's overall facial features.

In any event, the resultant of the prior art device is an "operated-on" appearance that is less than satisfactory for the patient and the doctor. These shortcomings are rectified by this invention by the use of hard-grade silicone and the special shape from the upper end to the tip, which shape includes a definite narrowing at the supra-tip region.

SUMMARY OF THE INVENTION

The nasal implant of this invention is characterized by a composition of hard-grade silicone fashioned into a special shape. One variation in the composition material is to use soft silicone only for the tip in order to overcome the fear of some surgeons to use hard silicone in this particular area.

The special and improved shape of the implant invention provides a well rounded and larger tip portion than that of the prior art. The supra-tip of this improved implant shows a depression dorsally, is less wide than the rest of the implant and has a pronounced slope laterally. These features, particularly at the supra-tip region avoid the parrot beak and unnatural effects. Moreover this implant invention has a variable thickness from upper end to tip—that is it starts thin, increases in thickness and then goes thinner again, whereas the prior art starts thin and continually increases throughout.

In the implant of this invention, the portion at the upper part, destined to lie between the eyes ("nasion"), has a rounded pointed end and shows a definite concavity dorsally and very reduced width laterally, compared to the main body portion at the bridge of the implant. These features enable the implant to blend well with the contour of the forehead of a patient. The implant of this invention does not present a straight line at the nasion as did the prior art.

This implant invention does not have a part going into the columella and thus is of the columella-less variety. In order to provide the support that is need at the tip, the invention has a large, well-rounded tip that is, at it's base where the tip joins the rest of the body, of an increased thickness. The tip's base (i.e. boundary of the supra-tip and bridge portion) is a large volume of hard-grade silicone which provides ample support for the tip. This ample support is clearly depicted in FIG. 4D which is a cross-sectional view of the junction at the supra-tip region and the bridge portion. Once the operation with an implant of this invention is completed, the skin and the implant's own weight does not cause the tip to turn down. The end result is a more pleasing look with a long-enduring support for the implant's tip.

These and other important features to be described in more detail in the following section concerning the detailed drawing description, achieve a natural look for the implant device of this invention.

BRIEF DESCRIPTION OF THE DRAWING

FIG. 1 depicts, in FIG. 1A, and 1B, two separate views of a typical prior art columella-less implant device;

FIG. 2 depicts, in FIG. 2A and 2B, another typical implant device of the columella type;

FIG. 3 depicts a plan view of a thin model of the invention;

FIG. 4 and FIGS. 4A through 4E depict the same device as FIG. 3 in side and cross-sectional views in order to promote a better understanding of the invention;

FIG. 5 depicts, in FIGS. 5A through 5D a side and cross-sectional views respectively of a "medium" nasal implant all in accordance with this invention.

FIG. 6 and FIGS. 6A through 6D depicts a side and cross-sectional views of a "thick" nasal implant device all in accordance with the invention;

FIG. 7 and FIG. 8 depict plan views of two different lengths in accordance with the invention with each plan view depicting the narrowing of the width at the supra-tip area.

DESCRIPTION OF THE PREFERRED EMBODIMENT

Described hereinafter is a nasal implant made of hard-grade silicone material of an improved design which allows a surgeon to more consistently obtain good aesthetic results. The improved implant is not conspicuous under the skin because the improved design and modified hourglass shape blends well with the natural bones and cartilage of the patient. The implant of the invention is provided in a variety of thicknesses and lengths to accommodate the wide variations in the shape and dimensions among noses. FIG. 3, however, depicts in general the plan view of all of the various shapes and dimensions. Comparison of FIG. 3 with FIGS. 7 and 8, which latter two figures are for two different lengths, show the similarity overall for the shape that has proven valuable for the invention.

FIG. 3 depicts a ventral plan view of the implant 25 which is termed herein as having a modified hourglass shape. Note that in FIG. 3 the bridge part, 35, is the widest dimension and after that the implant narrows down considerably to 40 and then again increases in width near the tip 50. This shape in the 35-40-50 area is typically referred to as an hourglass shape. It is called a "modified" hourglass herein because it does not have an extremely restricted neck portion that is typically associated with an hourglass. The modified hourglass shape may be better appreciated by looking at cross-sectional views 4A through 4D in FIG. 4 of this invention.

Implant 25, in FIG. 4, is shown in side view and includes a slightly thinner upper end 30 that is shaped so that the implant blends well and is naturally looking in the nasion area between the eyes. Some of the prior art implants in the nasion area are of essentially the same thickness and/or width as the rest of the implant body so that they create an undesirable shape and impression at the nasion. In the prior art, for example, the implant created an abrupt transition from the forehead to the beginning of the nose and that abrupt transition in the finished operation is unsightly. This nasion problem area is eliminated by the thin and narrow upper end 30 of the implant of this invention.

As is clearly shown in FIG. 4, the implant has been sectioned along its length by the horizontal section line such as 4A—4A in the side view of FIG. 4. For illustration purposes the length of the implant has been divided into about five equal sections which are labeled as shown at the sectional lines indicated by the letters 4A, 4B, 4C, 4D, and 4E. At each of the sectional line locations a corresponding end view is shown so that the variable thickness of the concave hollowed-out underside of the implant may be understood. The hollowed-out section 45, shown in dashed lines in the side view of FIG. 4, begins at the area where the tip base blends into the bridge portion 35. The bridge portion 35 constitutes the main body section of the improved implant and it has the widest dimension as shown in the plan view of FIG. 3.

Prior art implants often show as an unnatural implant because they do not sit well over the patient's nose bone and the patient's cartilage which is located lower down on the nose. The nose bone is sometimes at a different level than the cartilage that is generally positioned over the patient's nasal cavity. These different levels must be accommodated for, while still providing an implant with enough body support to hold a natural position and present enough contour from the nose bone to the implant's tip that a pleasing and natural finished look is provided. Use of this implant shape assures that the operation, when finished, looks natural and does not present the "operated on" look of the prior art. The implant of this invention has a tapered pointed nasion end 30 that is slightly concave dorsally as is shown in the view of FIG. 4. FIG. 4A depicts that the upper dorsal section is rounded and slopes away from the dorsal ridge of the implant.

The prior art implants usually are somewhat visible under the skin because their dorsal contour is a straight line or a flat surface and their width is somewhat the same from one end to the other. In the improved implant 25, the subtle variation in thickness and width in its different sectional parts (from end 30 through 4E) corresponds to the variation in the thickness of the skin and in the shape of the patient's bone and cartilage at different levels. Thus, the desirable purpose of hiding the implant of this invention can be achieved due primarily to its novel shape and tip-supporting feature.

The most important cross-sectional depth of cavity 45 is at the sections 4B to 4C. These sections define a far more pronounced cavity than anything known about in the prior art. The depth of these sections and the sloping outer tapered edges formed by the rounded dorsal shape cause the implant to sit well over the under-supporting cartilage and bone of a patient. These features contribute to the total implant design and are essential to the provision of a more natural looking result after surgery.

Cross-section 4D is at the area of the supra-tip to the tip region and this area, it is important to note, is narrow but possesses considerable depth. Just forward of section 4D is an under-cut recess 42. At the region of 4D, the cavity 45 has terminated and at this point the implant has its greatest thickness and the largest volume of the hard-grade silicone material used for the implant of this invention. It is also at this sectional area 4D that the hard-grade silicone is providing the extra support that is needed to hold the tip in its desired location after the implant has been used for the patient's operation. In the prior art that area was subject to two problems: one, the patient's cartilage itself sags under the weight and the skin's pressure and two, the soft silicone of the prior art would bend downwardly, particularly in the columella-less variety. These factors in the prior art created a parrot's beak look in that the supra-tip tends to be at a higher location than the tip of the nose. This defect has been remedied in the improved implant 25 because the tip 50 is full and well rounded and the concave dorsal portion 52, FIG. 4, from the supra-tip to the tip assures that the tip 52 will always be higher than the supra-tip area. Moreover, the increased hardness of the material and the increased volume of that material at section 4D assures good tip support in the finished operation.

Tip 50 is smooth, full and well rounded on its forward surface to minimize any damage to the covering skin and also to provide a pleasing contour to the tip. Tip 50 does not have any part that goes into the columella and this fact provides a freedom from the distortion that the smaller part of the L often creates in the prior art implants. A rounded undercut 42 is located at the underside of the tip 50 and this undercut 42 tapers from the forward part of the tip 50 back toward the section 4D. Note that the undercut 42 slopes to the location that provides the large volume of hard-grade silicone which I have provided in order to assure maximum support for tip 50.

On the opposed and ventral surface away from the undercut 42 I provide, in my improved implant 25, a pronounced slope 52 to a narrowed width 40 at the center of the somewhat hour-glass shaped plan view of implant 25. This narrowest width at the supra-tip location provides a tip that is natural and pleasing to the eye. Although the entire body including the tip is preferably made of hard-grade silicone, the tip 50 may at the forward and bulb part be comprised of a soft silicone to satisfy some doctor's concern over the use of hard-grade silicone of my invention. In this latter instance the section 4D is still to be composed of hard-grade silicone, however, so that the necessary tip support is available for the more pleasing implant of this invention.

FIGS. 5 and 6 are self explanatory in view of the foregoing description and thus do not require any detailed description. Suffice it to say that these two additional figures indicate the same useful features of my invention and are necessary because it is common to supply several general sizes for implant devices. Likewise FIGS. 7 and 8 show two other preferred lengths of an implant shaped and constructed in accordance with this invention in order to accommodate the wide variation of patient's noses. As described herein the implants are either 45 mm, 50 mm, or 55 mm in length. In each instance the implant shape and features as described above will be provided to assure a more natural and pleasing result. Although the drawing do not attempt to show scale figures, the essential features of my invention are therein presented.

In FIG. 3 some typical dimensions are given for an implant that is 50 mm long. Note that the plan view shows a slightly hour-glass shape for the implant 25. The area of the supra-tip has a width that is less by a couple of millimeters (mm) than the widest part of the implant at the bridge part 35 of the implant 25. For example the widest part may be on the order of 9 mm while the supra-tip width may be on the order of 7 mm. The result is a more natural looking finished operation using the implant 25.

The above description presents the best mode contemplated in carrying out my invention. My invention is, however, susceptible to modifications and alternate constructions from the embodiments shown in the drawings and described above. Consequently, it is not the intention to limit the invention to the particular embodiments disclosed. On the contrary, the invention is intended and shall cover all modifications, sizes and alternate constructions falling within the spirit and scope of the invention, as expressed in the appended claims when read in light of the description and drawings.

What is claimed is:

1. An improved columella-less nasal implant that is comprised of silicone and further comprising dorsal and ventral surfaces, said implant having, when viewed in a ventral plan view,
   an ;elongated bridge portion having essentially an hourglass shape, said hourglass shape including a middle portion and upper and lower ends, said middle portion defining a supra-tip region and said lower end defining a rounded tip portion;
   a pointed, thin nasion end designed for the eye region of the patient and extending from said upper end of said bridge portion and tapering outwardly therefrom;
   said supra-tip region of said implant having the largest volume and thickest depth dimension of the implant in order to achieve strong support for said rounded tip portion, said rounded tip portion having an upward slope at said ventral surface between the supra-tip region and said rounded tip portion thereby preventing the tip from turning downward.

2. An implant in accordance with claim 1, said implant, when viewed in a ventral plan view, having its narrowest dimension at said pointed nasion end, said implant having its widest dimension at said upper end of said bridge portion, narrowing again at the supra-tip region and widening again to form said lower end of said bridge portion at said rounded tip, said dimensions at said upper end of said bridge portion, the supra-tip region and said lower end of said bridge portion defining said hourglass shape, which shape provides a more natural looking implant for the patient.

3. An implant in accordance with claim 1 wherein said ventral surface at said bridge portion further comprises a convex portion and said dorsal surface at said rounded tip portion is sloped in a direction dorsally from the rounded tip end portion toward said thickest depth dimension.

4. An implant in accordance with claim 3 wherein said dorsal surface at said bridge portion comprises
   an elongated centrally located cavity having a depth selected to essentially receive a bridge bone and cartilage of the patient's nose.

5. An implant in accordance with claim 4 wherein the cavity when viewed in transverse cross-section, comprises:
   tapered sides and said cavity gradually diminishing in transverse cross-sectional area in a direction toward said lower end of said bridge portion and terminating at about the supra-tip region.

6. An implant in accordance with claim 1 wherein said implant is made of hard-grade silicone.

7. An implant device in accordance with claim 1 comprised in part of hard-grade silicone, and further comprising:
   a soft-grade silicone material forming the tip portion of said implant device, with said soft-grade tip blending into hard-grade silicone at the junction of said supra-tip region.

* * * * *